(12) United States Patent
Mesangeau et al.

(10) Patent No.: US 8,937,066 B2
(45) Date of Patent: Jan. 20, 2015

(54) AMINO DERIVATIVES OF DIHYDRO-1,3,5-TRIAZINE USED IN THE TREATMENT OF ISCHEMIA AND/OR REPERFUSION RELATED DISEASES

(75) Inventors: Didier Mesangeau, Combs la Ville (FR); Xavier Leverve, La Terrasse (FR); Daniel Cravo, Montesson (FR); Catherine Noe, legal representative, La Terrasse (FR)

(73) Assignees: Poxel, Lyons (FR); INSERM (Institut National de la Sante et de la Recherche Medicale), Paris Cedex (FR)

( * ) Notice: Subject to any disclaimer, the term of this patent is extended or adjusted under 35 U.S.C. 154(b) by 104 days.

(21) Appl. No.: 13/384,249

(22) PCT Filed: Jul. 16, 2010

(86) PCT No.: PCT/EP2010/060292
§ 371 (c)(1),
(2), (4) Date: Jan. 16, 2012

(87) PCT Pub. No.: WO2011/006984
PCT Pub. Date: Jan. 20, 2011

(65) Prior Publication Data
US 2012/0122873 A1   May 17, 2012

(30) Foreign Application Priority Data
Jul. 17, 2009 (FR) ...................................... 09 54977

(51) Int. Cl.
*A61K 31/53* (2006.01)
*A61P 9/10* (2006.01)

(52) U.S. Cl.
CPC ..................................... *A61K 31/53* (2013.01)
USPC ........................... 514/245; 544/204; 544/205

(58) Field of Classification Search
CPC ..................................................... A61K 31/53

USPC .................................... 514/245; 544/204, 205
See application file for complete search history.

(56) References Cited

U.S. PATENT DOCUMENTS

| 7,034,021 | B2 * | 4/2006 | Moinet et al. ................. 514/245 |
| 7,452,883 | B2 * | 11/2008 | Moinet et al. ................. 514/245 |
| 7,767,676 | B2 * | 8/2010 | Moinet et al. ................. 514/245 |
| 2003/0109530 | A1 | 6/2003 | Moinet et al. |
| 2006/0223803 | A1 | 10/2006 | Moinet et al. |
| 2011/0236317 | A1 * | 9/2011 | Cravo et al. .................... 424/9.2 |

FOREIGN PATENT DOCUMENTS

| EP | 1247809 | 10/2002 |
| FR | 2853650 | 10/2004 |
| FR | 2896159 | 7/2007 |
| WO | WO 01/36454 | 5/2001 |
| WO | WO 01/55122 | 8/2001 |
| WO | WO 2007/079917 | 7/2007 |
| WO | WO 2009/049157 | 4/2009 |
| WO | WO 2010/066901 | 6/2010 |

OTHER PUBLICATIONS

Kudo et al. J. Biol. Chem. 1995, 270 (29), 17513-17520.*
Bhamra et al. Basic Res. Cardiol. 2008, 103, 274-284.*
Bucciarelli et al. Circulation 2006, 113, 1226-1234.*
Ma, X. et al. "Synthesis and in vitro evaluation of 2,4-diamino-1,3,5-triazine derivatives as neuronal voltage-gated sodium channel blockers" *Bioorganic & Medicinal Chemistry Letters*, 2009, pp. 5644-5647, vol. 19.
Written Opinion in International Application No. PCT/EP2010/060292, Oct. 21, 2010, pp. 1-7.

* cited by examiner

*Primary Examiner* — Sreeni Padmanabhan
*Assistant Examiner* — Irina Neagu
(74) *Attorney, Agent, or Firm* — Saliwanchik, Lloyd & Eisenschenk

(57) ABSTRACT

The invention relates to amino derivatives of dihydro-1,3,5-triazine, used for the treatment and/or prevention of diseases induced by ischemia and/or reperfusion, notably cardiac and renal complications.

8 Claims, 2 Drawing Sheets

Figure 1:
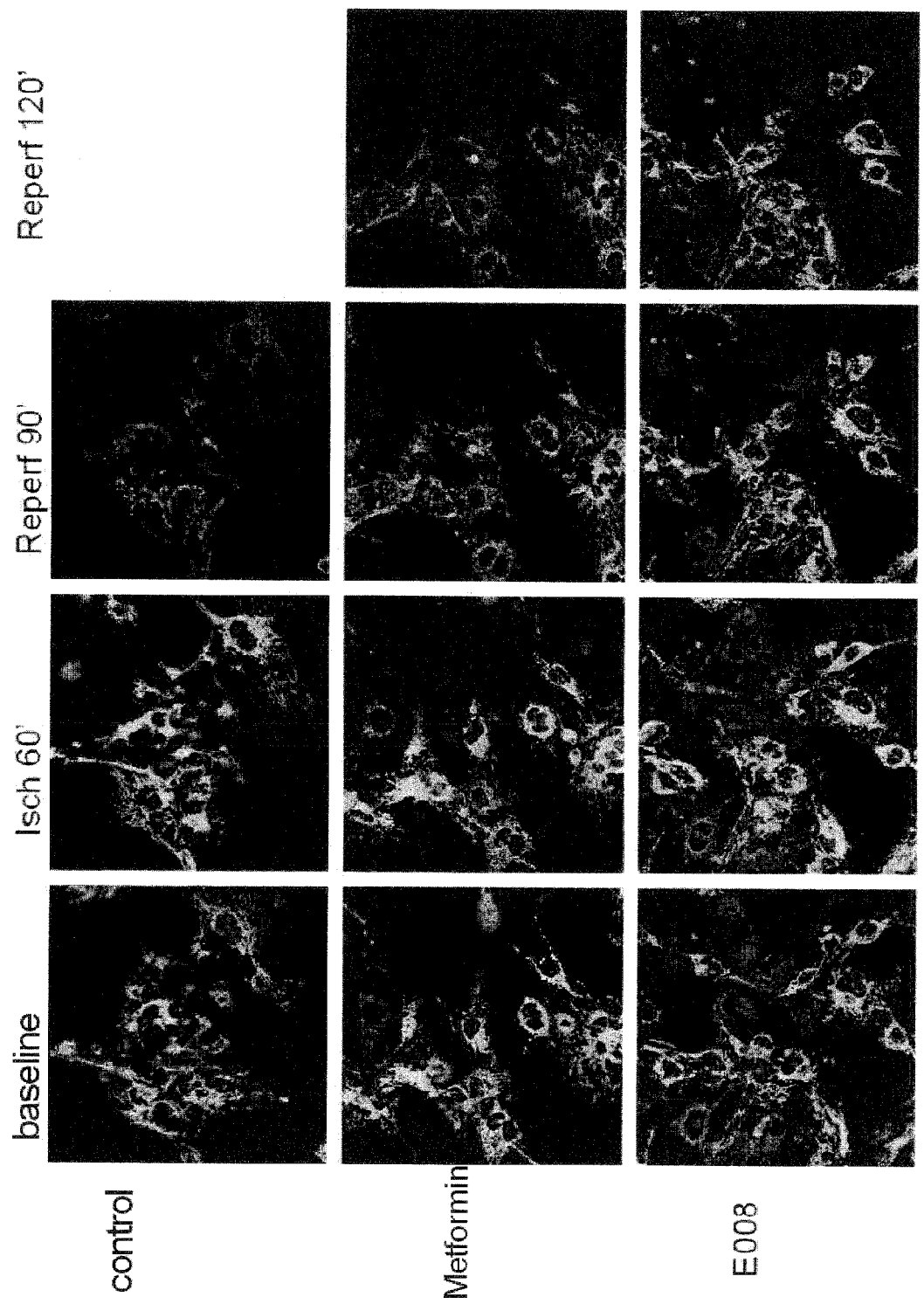

AMINO DERIVATIVES OF DIHYDRO-1,3,5-TRIAZINE USED IN THE TREATMENT OF ISCHEMIA AND/OR REPERFUSION RELATED DISEASES

CROSS-REFERENCE TO RELATED APPLICATION

This application is the U.S. national stage application of International Patent Application No. PCT/EP2010/060292, filed Jul. 16, 2010, the disclosure of which is hereby incorporated by reference in its entirety, including all figures, tables and amino acid or nucleic acid sequences.

The invention claimed in this application arose as a result of activities undertaken within the scope of a joint research agreement and was made by or behalf of parties to a joint research agreement in effect on, or before, the date the claimed invention was made. The parties to the joint research agreement were Merck Sante and INSERM (Institut National de la Sante et de la Recherche Medicale).

FIELD OF THE INVENTION

The invention relates to amino derivatives of dihydro-1,3,5-triazine, used for the treatment and/or prevention of diseases induced by ischemia and/or reperfusion, notably cardiac and renal complications.

TECHNICAL BACKGROUND

Myocardial ischemias are defined as an imbalance between oxygen needs and supply. This imbalance leads to a disorder of cardiac function. In the vast majority of cases, myocardial ischemias are caused by an insufficiency of blood circulation to the heart muscle tissue, thus depriving the myocardial cells of their oxygen supply or drastically decreasing said supply. These ischemias may be due to obstruction of a vessel (thrombosis), reduction of the inside diameter of an artery (stenosis), or a decrease in coronary blood flow (hypoperfusion) such as in states of circulatory failure associated with severe sepsis with endotoxemic shock. In this connection, it should be noted that severe sepsis also leads to hemodynamic dysfunction with direct myocardial depression. At present, however, it is not clear which mechanism is predominant in reduction of myocardial function, hypoperfusion or myocardial depression by circulating cytokines.

Infarction is one of the major consequences of ischemias. The term infarction describes a localized area of tissue necrosis. Thus, myocardial infarction leads to destruction of a portion of the heart owing to the death of cells of the heart muscle. Myocardial infarction is a very common event. For example, it is estimated that, in France, about 180 000 to 200 000 persons per year, predominantly men, are affected by this disease. It occurs in particular in subjects having cardiovascular risk factors such as use of tobacco, obesity, diabetes, hyperlipidemia or arterial hypertension. The extent of myocardial infarction is a determining element for contractile functional recovery of the myocardium and patients' long-term prognosis.

Acute myocardial infarction (AMI) constitutes an absolute cardiological emergency which requires management by specialized medical and hospital services with treatment of the acute phase with the aim of reperfusing the ischemic heart muscle and of preventing and/or limiting the possible complications associated with infarction that frequently lead to patient death in the first hours or the first days.

Reperfusion is defined as the reestablishment of adequate blood circulation within an ischemic tissue, so that a balance can be achieved again between oxygen needs and supply. Reperfusion in the case of complete interruption of coronary blood flow is generally carried out by clearing the occluded artery.

Although reperfusion undoubtedly protects myocardial cells against cell death caused by persistence of ischemia, it is also accompanied by adverse effects on contractile function (myocardial stunning), cardiac rhythm (occurrence of arrhythmias) and tissue perfusion ("no-reflow"). Recent data even indicate that reperfusion can also, paradoxically, kill some of the reperfused cells (reperfusion necrosis).

During reperfusion of myocardial infarction, drugs belonging to various therapeutic classes, for example antiplatelet agents such as acetylsalicylic acid, beta-blockers, converting enzyme inhibitors (CEIs) or statins have a beneficial effect on patients' prognosis. However, none of these drugs or other drugs currently available, administered during reperfusion, is able to limit the size of the myocardial infarct.

An ischemic situation can also lead to a change of normal function of other organs such as the kidney (Zhao, Jing; Dong, et al. Guoji Bingli Kexue Yu Linchuang Zazhi (2007), 27(6), 539-544) or the brain (Zhu, Xia-Ling, Neuroscience Letters, 2009).

Moreover, amino derivatives of dihydro-1,3,5-triazine of the following general formula (I) are known from European patent EP 1 250 328:

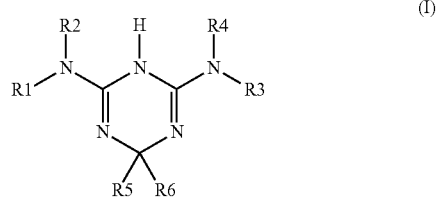

It was demonstrated that these compounds display antidiabetic activity in an experimental model of noninsulin-dependent diabetes, induced in rats by streptozotocin.

The present invention results from the unexpected demonstration, by the inventors, that the amino derivatives of dihydro-1,3,5-triazine of formula (I) make it possible to improve the treatment and/or prevention of diseases associated with ischemia and/or reperfusion, notably cardiac and renal complications. More particularly, it was demonstrated that the compound E 008 made it possible to reduce the production of ROS by complex I of the respiratory chain of endothelial cells, by inhibiting reverse electron flow. Moreover, this compound can prevent loss of mitochondrial membrane potential and can reduce the opening of the mitochondrial permeability transition pore (PTP), notably during ischemia and/or reperfusion events.

The present invention thus relates to a compound of general formula (I):

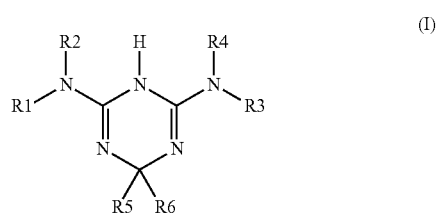

in which:
R1, R2, R3, and R4 are selected independently from the groups:

—H,
alkyl (C1-C20) unsubstituted, or substituted with halogen, alkyl (C1-C5), alkoxy (C1-C5), cycloalkyl (C3-C8), alkenyl (C2-C20) unsubstituted, or substituted with halogen, alkyl (C1-C5), alkoxy (C1-C5), alkyne (C2-C20) unsubstituted, or substituted with halogen, alkyl (C1-C5), alkoxy (C1-C5), cycloalkyl (C3-C8) unsubstituted, or substituted with alkyl (C1-C5), alkoxy (C1-C5), heterocycloalkyl (C3-C8) bearing one or more heteroatoms selected from N, O, S and unsubstituted, or substituted with alkyl (C1-C5), alkoxy (C1-C5), aryl (C6-C14) alkyl (C1-C20) unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, aryl (C6-C14) unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, heteroaryl (C1-C13) bearing one or more heteroatoms selected from N, O, S and unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, R1 and R2, on the one hand, and R3 and R4, on the other hand, which can form, with the nitrogen atom, a ring with n ring members (n between 3 and 8) comprising or not comprising one or more heteroatoms selected from N, O, S and which can be substituted with one or more of the following groups: amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, R5 and R6 are selected independently from the groups:
H,
alkyl (C1-C20) unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, alkenyl (C2-C20) unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, alkynyl (C2-C20) unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, cycloalkyl (C3-C8) unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, heterocycloalkyl (C3-C8) bearing one or more heteroatoms selected from N, O, S and unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, aryl (C6-C14) unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, heteroaryl (C1-C13) bearing one or more heteroatoms selected from N, O, S and unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, aryl (C6-C14) alkyl (C1-C5) unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, and R5 and R6 can form, with the carbon atom to which they are attached, a ring with m ring members (m between 3 and 8) comprising or not comprising one or more heteroatoms selected from N, O, S and which can be substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, or which can form, with the carbon atom, a C10-C30 polycyclic residue unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl, and R5 and R6 can also represent together the group =O or =S, moreover the nitrogen atom of a heterocycloalkyl or heteroaryl group can be substituted with an alkyl (C1-C5), cycloalkyl (C3-C8), aryl (C6-C14), aryl (C6-C14) alkyl (C1-C5) or acyl (C1-C6) group, as well as the tautomeric, enantiomeric, diastereoisomeric and epimeric forms and the pharmaceutically acceptable salts, for use in the treatment and/or prevention of lesions, disorders or diseases associated with ischemia and/or reperfusion.

The present invention also relates to the use of a compound of formula (I) as defined above, for preparing a drug intended for the prevention and/or treatment of a lesion, a disorder or a disease associated with ischemia and/or reperfusion.

The present invention also relates to a method of prevention and/or treatment of a pathology associated with ischemia and/or reperfusion in a patient, in which a prophylactically or therapeutically effective amount of a compound of formula (I) as defined above is administered to said patient.

DETAILED DESCRIPTION OF THE INVENTION

"Ring with m ring members formed by R5 and R6" means in particular a saturated ring such as a cyclohexyl, piperidinyl or tetrahydropyrannyl group.

"Polycyclic group formed by R5 and R6" means a carbon-containing polycyclic group, optionally substituted, and in particular a steroid residue.

A particular group of compounds of formula (I) is that in which R5 is hydrogen.

Another particular group of compounds of formula (I) is that in which R5 and R6 form, with the carbon atom to which they are attached, a ring with m ring members (m between 3 and 8), comprising or not comprising one or more heteroatoms selected from N, O, S and which can be substituted with one or more of the following groups:

alkyl (C1-C5), amino, hydroxy, alkylamino (C1-C5), alkoxy (C1-C5), alkylthio (C1-C5), aryl (C6-C14), aryl (C6-C14)-alkoxy (C1-C5), or form, with the carbon atom, a C10-C30 polycyclic residue, unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl.

Another particular group of compounds of formula (I) is that in which R5 and R6 are selected independently from the groups:

alkyl (C1-C20) unsubstituted, or substituted with amino, hydroxy, thio, halogen, alkyl (C1-C5), alkoxy (C1-C5), alkylthio (C1-C5), alkylamino (C1-C5), aryl (C6-C14) oxy, aryl (C6-C14) alkoxy (C1-C5), cyano, trifluoromethyl, carboxy, carboxymethyl or carboxyethyl.

The invention also relates to the tautomeric forms, to the enantiomers, diastereoisomers, epimers and to the organic or mineral salts of the compounds of general formula (I).

The compounds of the invention of formula (I) as defined above possessing a sufficiently acid function or a sufficiently basic function or both, can include the corresponding pharmaceutically acceptable salts of organic or mineral acid or of organic or mineral base.

In particular, the compounds of general formula (I) possess basic nitrogen atoms, which can be monosalified or disalified by organic or mineral acids.

Preferably, the compound according to the invention is in the form of hydrochloride.

Preferably, R6 is a (C1-C20)alkyl group, notably a methyl group.

Preferably, R1 and/or R2 represents/represent a (C1-C20) alkyl group, notably a methyl group.

Preferably, R3 and/or R4 represents/represent a hydrogen atom.

Preferably, R1 and R2 are a methyl group and R3 and R4 represent a hydrogen.

Among the preferred compounds of formula (I), we may notably mention the compound E 008 of formula (Ia):

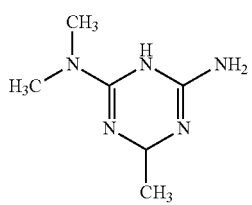

(Ia)

as well as its tautomeric, enantiomeric, diastereoisomeric and epimeric forms and/or pharmaceutically acceptable salts.

In a preferred embodiment of the invention, the compound of general formula (I) is (+) 5,6-dihydro-4-dimethylamino-2-imino-6-methyl-1,3,5-triazine or its hydrochloride.

In a preferred embodiment of the invention, the compound of general formula (I) is (−) 5,6-dihydro-4-dimethylamino-2-imino-6-methyl-1,3,5-triazine or its hydrochloride.

According to another aspect, the invention relates to a compound of formula (I) as defined above for use in the treatment and/or prevention of diseases associated with ischemia and/or reperfusion, notably cardiac or renal complications. As examples of cardiac pathologies, we may notably mention cardiac arrhythmia, myocardial infarction or heart attack.

According to the present invention, "alkyl" radicals represent saturated hydrocarbon radicals, linear or branched, with 1 to 20 carbon atoms, preferably with 1 to 5 carbon atoms. We may notably mention, when they are linear, the methyl, ethyl, propyl, butyl, pentyl, hexyl, octyl, nonyl, decyl, dodecyl, hexadecyl, and octadecyl radicals. We may notably mention, when they are branched or substituted with one or more alkyl radicals, the isopropyl, tert-butyl, 2-ethylhexyl, 2-methylbutyl, 2-methylpentyl, 1-methylpentyl or 3-methylheptyl radicals.

The "alkoxy" radicals according to the present invention are radicals of formula —O-alkyl, alkyl being as defined previously.

"Alkylthio" denotes an alkyl-S— group, the alkyl group being as defined above.

"Alkylamino" denotes an alkyl-NH— group, the alkyl group being as defined above.

Among the halogen atoms, we may more particularly mention the fluorine, chlorine, bromine and iodine atoms.

The "alkenyl" radicals represent hydrocarbon radicals, straight-chain or linear, and comprise one or more ethylenic unsaturations. Among the alkenyl radicals, we may notably mention the allyl or vinyl radical.

The "alkynyl" radicals represent hydrocarbon radicals, straight-chain or linear, and comprise one or more acetylenic unsaturations. Among the alkynyl radicals, we may notably mention the acetylene radical.

The "cycloalkyl" radical is a mono-, bi- or tri-cyclic hydrocarbon radical, saturated or partially unsaturated, nonaromatic, with 3 to 10 carbon atoms, such as notably cyclopropyl, cyclopentyl, cyclohexyl or adamantyl, as well as the corresponding rings containing one or more unsaturations.

The "heterocycloalkyl" radicals denote mono- or bicyclic systems, saturated or partially unsaturated, nonaromatic, with 3 to 8 carbon atoms, comprising one or more heteroatoms selected from N, O or S.

"Aryl" denotes an aromatic hydrocarbon system, mono- or bicyclic, with 6 to 10 carbon atoms. Among the aryl radicals, we may notably mention the phenyl or naphthyl radical, more particularly substituted with at least one halogen atom.

The "arylalkyl" or "aralkyl" radicals are aryl-alkyl- radicals, the aryl and alkyl groups being as defined above. Among the aralkyl radicals, we may notably mention the benzyl or phenethyl radical.

"Aryloxy" denotes an aryl-O— group, the aryl group being as defined above.

"Arylalkoxy" denotes an aryl-alkoxy- group, the aryl and alkoxy groups being as defined above.

The "heteroaryl" radicals denote aromatic systems comprising one or more heteroatoms selected from nitrogen, oxygen or sulfur, mono- or bicyclic, with 5 to 10 carbon atoms. Among the heteroaryl radicals, we may mention pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]pyridine, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzoazaindole, 1,2,4-triazinyl, benzothiazolyl, furanyl, imidazolyl, indolyl, triazolyl, tetrazolyl, indolizinyl, isoxazolyl, isoquinolinyl, isothiazolyl, oxadiazolyl, pyrazinyl, pyridazinyl, pyrazolyl, pyridyl, pyrimidinyl, purinyl, quinasolinyl, quinolinyl, isoquinolyl, 1,3,4-thiadiazolyl, thiazolyl, triazinyl, isothiazolyl, carbazolyl, as well as the corresponding groups resulting from their fusion with one another or with the phenyl nucleus.

"Carboxyalkyl" denotes an HOOC-alkyl- group, the alkyl group being as defined above. As examples of carboxylalkyl groups, we may notably mention carboxymethyl or carboxyethyl.

The expression "pharmaceutically acceptable salts" refers to salts of acid addition that are relatively nontoxic, inorganic and organic, and to the salts of addition with a base, of the compounds of the present invention. These salts can be prepared in situ during final isolation and purification of the compounds. In particular, the salts of acid addition can be prepared by separately reacting the purified compound in its purified form with an organic or inorganic acid and isolating the salt thus formed. Examples of salts of acid addition include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptanate, lactobionate, sulfamate, malonate, salicylate, propionate, methylenebis-b-hydroxynaphthoate, gentisic acid, isethionate, di-p-toluoyltartrate, methanesulfonate, ethanesulfonate, benzenesulfonate, p-toluenesulfonate, cyclohexyl sulfamate and quinateslaurylsulfonate salts, and analogs (see for example S. M. Berge et al. "Pharmaceutical Salts" *J. Pharm. Sci*, 66: p. 1-19 (1977)). The salts of acid addition can also be prepared by separately reacting the purified compound in its acid form with an organic or inorganic base and isolating the salt thus formed. The salts of acid addition comprise the amino and metal salts. Suitable metal salts comprise the sodium, potassium, calcium, barium, zinc, magnesium and aluminum salts. The sodium and potassium salts are preferred. Suitable inorganic salts of addition of a base are prepared from metallic bases that comprise sodium hydride, sodium hydroxide, potassium hydroxide, calcium hydroxide, aluminum hydroxide, lithium hydroxide, magnesium hydroxide, zinc hydroxide. Suitable amino salts of addition of a base are prepared from amines that have sufficient alkalinity to form a stable salt, and preferably comprise the amines that are often used in medicinal chemistry on account of their low toxicity and their acceptability for medical use: ammonia, ethylenediamine, N-methyl-glucamine, lysine, arginine, ornithine, choline, N,N'-dibenzylethylenediamine, chloroprocaine, diethanolamine, procaine, N-benzyl-phenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, for example lysine and arginine, and dicyclohexylamine, and analogs.

The compounds of general formula (I) can be prepared by application or adaptation of any method known per se and/or within the capacity of a person skilled in the art, notably those described by Larock in *Comprehensive Organic Transformations*, VCH Pub., 1989, or by application or adaptation of the methods described in EP 1 250 328.

The pharmaceutical compounds according to the invention can be presented in forms intended for administration by the parenteral, oral, rectal, permucosal or percutaneous route.

The pharmaceutical compositions including these compounds of formula (I) will therefore be presented in the form of solutes or injectable suspensions or multi-dose bottles, in the form of bare or coated tablets, sugar-coated pills, capsules, pills, cachets, powders, suppositories or rectal capsules, solutions or suspensions, for percutaneous use in a polar solvent, for permucosal use.

The excipients that are suitable for these dosage forms are the derivatives of cellulose or of microcrystalline cellulose, alkaline-earth carbonates, magnesium phosphate, starches, modified starches, lactose for the solid forms.

For rectal use, cocoa butter or polyethylene glycol stearates are the preferred excipients.

For parenteral use, water, aqueous solutes, physiological serum, and isotonic solutes are the vehicles most often used.

The posology can vary over a wide range (0.5 mg to 1000 mg) depending on the therapeutic indication and the route of administration, as well as the subject's age and weight.

The expression "lesions, disorders or diseases associated with ischemia-reperfusion" denotes all lesions, disorders or diseases that are caused or maintained, at least partially, as a result of ischemia and/or reperfusion. It also denotes lesions, disorders or diseases that are the consequence of an ischemic and/or reperfusion event.

Preferably, the compounds of formula (I) according to the invention are useful for the treatment and/or prevention of cardiac complications, notably of cardiac arrhythmia, myocardial infarction or cardiac hypertrophy, the latter generally inducing heart failure.

According to another preferred embodiment, the compounds of formula (I) are useful for the treatment or prevention of renal complications.

According to yet another preferred embodiment, the compounds of formula (I) are useful for the treatment or prevention of cerebral complications, notably cerebrovascular accidents (CVAs).

In the context of the invention, the term "treatment" denotes preventive, therapeutic, palliative treatment, as well as management of patients, reduction of suffering, improvement of life span, improvement of quality of life, or slowing of progression of the disease.

FIGURES

FIG. 1 shows mitochondrial cells, untreated (control), or treated with metformin or E 008, incubated with the fluorescent probe tetramethylrhodamine methyl ester (TMRM) and observed in confocal microscopy: before treatment (baseline), after 60 min of ischemia (Isch 60'), after 90 min of reperfusion (Reperf 90') and after 120 min of reperfusion (Reperf 120') (FIG. 1).

Figure 2:
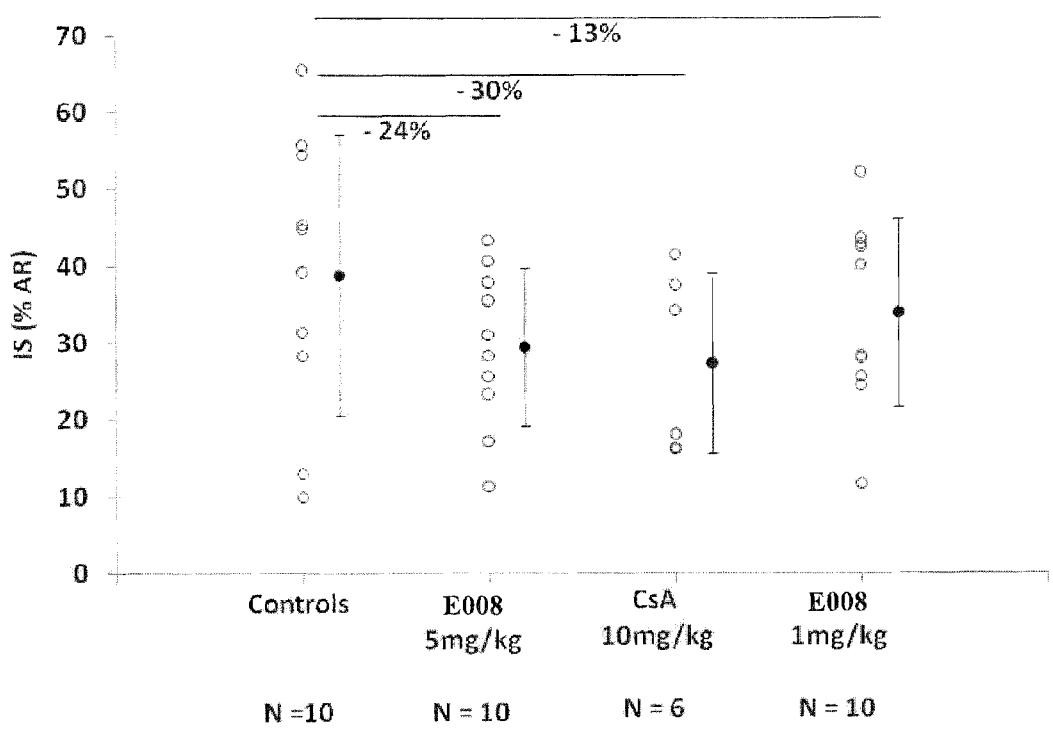

FIG. 2 shows the infarct size relative to the size of the area at risk as a function of the treatment administered to the rabbits in the model of myocardial infarction.

The following examples are supplied for illustrating the invention and must in no case be regarded as limiting the scope of the invention.

EXAMPLES

Example 1

Evaluation of the Protective Effect of E 008 on Vascular Injury Due to Ischemia/Reperfusion The objective of this study is to evaluate the protective effect of the compound E 008 on vascular injury due to ischemia/reperfusion, by measuring the effect of E 008 on loss of mitochondrial membrane potential induced by ischemia/reperfusion.

Material and Methods
Cell Culture
The line of human immortalized microvascular dermal endothelial cells HMEC-1 was used.
Treatment
The cells were treated according to the following scheme:
control group: no treatment, followed by ischemia of 60 min and reperfusion of 120 min.
metformin group: incubation with metformin at a concentration of 10 mM for 30 min, followed by ischemia of 60 min and reperfusion of 120 min.
E 008 group: incubation with the compound E 008 at a concentration of 10 mM for 30 min followed by ischemia of 60 min and reperfusion of 120 min.
Measurement of Mitochondrial Membrane Potential
In order to measure the mitochondrial potential, the cells were incubated, throughout the above treatment, with the fluorescent probe tetramethylrhodamine methyl ester (TMRM) at a concentration of 30 nM.
They were analyzed in confocal microscopy before treatment, after 60 min of ischemia, after 90 min of reperfusion and after 120 min of reperfusion (FIG. 1).
Results
In the control group and in the treated groups, the period of ischemia did not alter the mitochondrial membrane potential.
However, reperfusion of 90 min caused a large loss of mitochondrial membrane potential in the control group. The membrane potential even disappeared after 120 min of reperfusion, which implies that the cells are dead.
In contrast, for the cells treated with metformin and E 008, their mitochondrial membrane potential was protected from the damage due to reperfusion. E 008 even displays a better protective effect against loss of membrane potential than metformin.
E 008 therefore displays a cellular protective effect after ischemia and reperfusion. In particular, this compound reduces the loss of mitochondrial membrane potential induced by ischemia. This observed effect could be due to the inhibitory effect of E 008 on the mitochondrial permeability transition pores (MPTPs), which reduces the opening of the MPTPs. These results demonstrate that E 008 might contribute to cardiac and renal protection after a phase of ischemia.

Example 2

Reduction of Infarct Size with E 008 in a Model of Myocardial Infarction in the Rabbit Protocol:
Surgical Preparation:
The study complies with the "*Guide for the Care and Use of Laboratory Animals*" published by the US National Institutes of Health (NIH Publication No. 85-23, revised 1996).
Male New Zealand albino rabbits weighing between 2.2 and 2.5 kg were anesthetized by intramuscular injection of xylazine (5 mg/kg) and ketamine (50 mg/kg). An intravenous infusion of a mixture of xylazine (20 to 50 µg/kg/min) and ketamine (40 to 100 µg/kg/min) was maintained throughout the test.
After a median cervical incision, a tracheotomy was performed and the animals were ventilated with ambient air. A cannula was inserted in the right internal jugular vein for administration of the medicinal products and fluids and in the left carotid artery for measurement of blood pressure. After an intravenous bolus administration of fentanyl (10 mg/kg), a left thoracotomy was performed at the level of the fourth left intercostal space. The pericardium was opened and the heart was exposed. A 3.0 suture thread attached to a small curved needle was passed around a marginal branch of the left circumflex coronary artery. The two ends of the thread were passed through a small vinyl tube to form a collar that could be tightened for occluding and released for reperfusing the artery. Body temperature was monitored via an intraperitoneal thermometer and kept constant by means of a heating block. The heart rate and arterial pressure were monitored continuously on a Gould recorder (Gould Inc., Cleveland, Ohio).
After surgery, a period of stabilization of 15 minutes was observed.
Treatment Protocol:
The rabbits are randomly distributed into 4 groups. All the animals undergo a prolonged occlusion of 30 minutes of the coronary artery, followed by 4 hours of reperfusion. Five minutes before reperfusion, the rabbits receive an intravenous injection of either:
a vehicle (volume corresponding to dose 1 or 2 of E 008) (Control, C),
E 008 at dose 1,
E 008 at dose 2,
of ciclosporin A (CsA) at 10 mg/kg.
The sample size is 8 to 10 animals per group. In these groups, the hearts were collected at the end of the period of 4 hours of reperfusion for subsequent evaluation of infarct size.
Determination of the Area at Risk and of Infarct Size
After 4 hours of reperfusion, the coronary artery was briefly reoccluded and 0.5 mg/kg of Uniperse blue pigment (Ciba-Geigy®, Hawthorne N.Y.) was injected intravenously for delimiting the area at risk in viva With this technique, the previously nonischemic myocardium appears blue, whereas the previously ischemic myocardium (area at risk) remains unstained.
The anesthetized rabbits were then euthanized by intravenous injection of pentobarbital. The heart was excised and cut into transverse slices with thickness of 5 to 6 mm, parallel to the atrioventricular sulcus. After removing the tissue of the right ventricle, each slice was weighed. The basal surface of each slice was photographed for later measurement of the area at risk. Each slice was then incubated for 15 minutes in a 1% solution of triphenyltetrazolium chloride at 37° C. for differentiating the myocardial zones that were infarcted (pale) and viable (brick red). The slices were then photographed again. Magnified projections of these slices were traced for determining the boundaries of the area at risk (AR) and of the area of necrosis (AN). The extent of these areas at risk and of necrosis was quantified by planimetry by computer and corrected relative to the weight of the tissue slices. The total weights of the area at risk and of the area of necrosis were then calculated and expressed in grams and as a percentage of total left ventricle (LV) and of the weight of the area at risk, respectively. Hearts for which the region at risk did not exceed 10% of the weight of the left ventricle were excluded from the study. Evaluation of infarct size was performed blind.
Results:
The results are presented in the following table in the form of value averaged for all the animals of a group, the figure in parentheses representing the extent of the values measured for the different animals.
AR: area at risk
AN: area of necrosis
LV: left ventricle

|  | AR (g) | AN (g) | AR/LV (%) | AN/AR (%) | AN/LV(%) |
|---|---|---|---|---|---|
| Control | 0.79 (±0.32) | 0.34 (±0.23) | 29.8 (±12.6) | 38.8 (±18.2) | 12.8 (±8.4) |
| E 008 1 mg/kg | 0.87 (±0.23) | 0.31 (±0.15) | 34.5 (±7.3) | 33.9 (±12.2) | 11.8 (±5) |
| E 008 5 mg/kg | 0.73 (±0.17) | 0.21 (±0.09) | 28.5 (±8.5) | 29.4 (±10.3) | 8.3 (±3.7) |
| CsA | 0.76 (±0.26) | 0.22 (±0.16) | 30 (±7.8) | 27.3 (±11.7) | 8.5 (±5.4) |

The results are also shown in FIG. 2.

The compound E 008 permits a significant reduction in infarct size relative to the control. The dose of 5 mg/kg even gives a reduction in infarct size relative to ciclosporin A. Thus, a dose of 5 mg/kg provides significant protection in this model of myocardial infarction.

The invention claimed is:

1. A method for the treatment of a lesion, a disorder or a disease associated with ischemia and/or reperfusion, comprising administration to a patient in need of such treatment of an effective amount of the compound of formula (Ia):

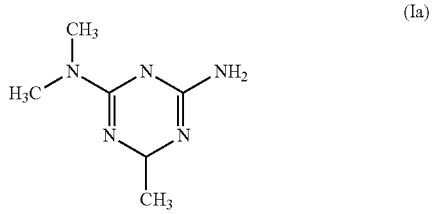

(Ia)

or tautomeric forms, enantiomeric forms, diastereoisomeric forms, epimeric forms or pharmaceutically acceptable salts thereof, and wherein the lesion, the disorder or the disease associated with ischemia and/or reperfusion is selected from the group consisting of cardiac complications, renal complications, and cerebral complications.

2. The method of claim 1, wherein the compound is (+) 5,6-dihydro-4-dimethylamino-2-imino-6-methyl-1,3,5-triazine or a pharmaceutically acceptable salt thereof.

3. The method of claim 1, wherein the compound is (−) 5,6-dihydro-4-dimethylamino-2-imino-6-methyl-1,3,5-triazine or a pharmaceutically acceptable salt thereof.

4. The method of claim 1, wherein the compound is in the form of a hydrochloride salt.

5. The method of claim 4, wherein the compound is a hydrochloride salt of (+) 5,6-dihydro-4-dimethylamino-2-imino-6-methyl-1,3,5-triazine.

6. The method of claim 4, wherein the compound is a hydrochloride salt of (−) 5,6-dihydro-4-dimethylamino-2-imino-6-methyl-1,3,5-triazine.

7. The method of claim 1, wherein the lesion, the disorder or the disease associated with ischemia and/or reperfusion is cardiac arrhythmia, myocardial infarction or cardiac hypertrophy inducing heart failure.

8. The method of claim 1, wherein the lesion, a disorder or a disease associated with ischemia and/or reperfusion is a cerebrovascular accident.

* * * * *

UNITED STATES PATENT AND TRADEMARK OFFICE
CERTIFICATE OF CORRECTION

| | | |
|---|---|---|
| PATENT NO. | : 8,937,066 B2 | Page 1 of 1 |
| APPLICATION NO. | : 13/384249 | |
| DATED | : January 20, 2015 | |
| INVENTOR(S) | : Didier Mesangeau et al. | |

It is certified that error appears in the above-identified patent and that said Letters Patent is hereby corrected as shown below:

Specification

Column 10,
Line 32, "in viva With" should read --in vivo. With--.

Signed and Sealed this
Sixth Day of October, 2015

Michelle K. Lee
*Director of the United States Patent and Trademark Office*